United States Patent [19]
Webber et al.

[11] Patent Number: 5,563,220
[45] Date of Patent: Oct. 8, 1996

[54] POLYMERIC RESIN FOR PEPTIDE SYNTHESIS

[75] Inventors: Robert Webber; Mohandas Pai, both of Berkeley, Calif.

[73] Assignee: Research & Diagnostic Antibodies, Berkeley, Calif.

[21] Appl. No.: 305,807

[22] Filed: Sep. 13, 1994

Related U.S. Application Data

[63] Continuation of Ser. No. 983,057, Nov. 30, 1992, abandoned, which is a continuation of Ser. No. 715,561, Jun. 14, 1991, Pat. No. 5,198,531.

[51] Int. Cl.$^6$ .................................................. C08F 8/32
[52] U.S. Cl. ........................... 525/333.3; 525/332.2; 525/333.4; 525/333.6; 525/379; 525/382
[58] Field of Search .......................... 525/333.3, 333.4, 525/333.6

[56] References Cited

PUBLICATIONS

"Stable Polyradicals," Chemical Abstract 69:52474, R.N. 28850-78-4, Braun et al., 1968.

"Polynucleotides," Hayatsu et al., J. Am. Chem. Soc., 89 (15), 3880-7, 1967.

*Primary Examiner*—Bernard Lipman
*Attorney, Agent, or Firm*—Bielen, Peterson & Lampe

[57] ABSTRACT

A polymeric resin for the preparation of peptides utilizing a polymeric matrix such as polystyrene-divinylbenzene copolymer. A vanillyl alcohol (HMBA), Trityl alcohol, or Trityl Amine group is attached to the polymeric carrier for use in the building of polypeptides by solid phase peptide synthesis employing the Fmoc protecting strategy.

7 Claims, No Drawings

POLYMERIC RESIN FOR PEPTIDE SYNTHESIS

This is a continuation of application Ser. No. 07/983,057, filed 30 Nov. 1992, now abandoned which is a continuation of application Ser. No. 07/715,561, filed 14 Jun. 1991 U.S. Pat. No. 5,198,531.

BACKGROUND OF THE INVENTION

The present invention relates to a novel polymeric resin and method suitable for use in creating polypeptides.

Solid phase peptide synthesis (SPPS) has proven to be the only practical method of producing synthetic peptides longer than 8–10 amino acids. One method of producing synthetic peptides is called Boc (tert-butyloxycarbonyl) SPPS. Another method of producing synthetic peptides is known as Fmoc (9-fluorenylmethyloxy carbonyl) SPPS. Both Boc and Fmoc SPPS employ minuscule spheres of specially produced resin which are suspended in a chemical solution. Each of these spheres serve as a anchor for the assembly of amino acid chains to produce polypeptides.

The Boc SPPS, although the most popular currently used method for the synthesis of peptides, suffers from low yield of product (especially with peptides of medium to long length), low purity, and an inability to build certain combinations of the amino acids except with great difficulty and expense. Specifically, trifluoroacetic (TFA), normally used to deprotect the amino terminal during each synthesis cycle in the Boc protection strategy, also cleaves approximately 1% of the resin anchor peptides from the resin spheres. Thus, yield and purity diminishes rapidly during the synthesis processes. The latter is a result of cleaved and lost chains leaving free initiation sites on the resin, thus permitting new chains to start building thereupon. Moreover, hydrofluoric acid (HF), an integral component of Boc SPPS, is responsible for many destructive side effects when applied to synthetic peptides.

Fmoc SPPS improves upon Boc SPPS in that an orthogonal synthesis system is employed. In other words, the side-chain blocking groups and the peptide-resin linkages are completely stable to the agents used during each step of the synthesis of peptides. Specifically, the deprotecting step of each cycle employs a secondary amine base which does not attack the bond between the growing peptide chain and resin support, since this bond is acid labile. Moreover, only TFA is used with Fmoc, eliminating the destructive side effects of HF. Some Fmoc SPPS, however, employs polyamide resin which generally possesses a low loading capacity. Present polyamide resins also tend to clump together rendering it impotent for large scale production.

Reference is made to U.S. Pat. Nos. 4,831,084 and 4,914,151 to Mergler et al which describes polystyrene resin-linker formulations which are usable in Fmoc SPPS. Unfortunately, the resin described in Mergler is difficult to prepare since the starting material must made by a multi-step reaction. In addition, the finished synthetic peptide is cleaved from the resin employing 1% TFA in dichloromethane (DCM). It has been found that 1% TFA is strong enough to remove a significant fraction of the side chain blocking groups, either Boc or triphenylmethyl (Trt). Boc is used to block the functional moiety on the side chains of the Lys, while Trt blocks Cys and His. Elimination of these amino acids from any peptide construction severely hinders applicability of the same. Also, the Mergler resin generally operates at a low level of substitution, thus, precluding large scale industrial processing. Making such resin with high loading characteristics, would be enormously costly since a starting material for this resin is expensive.

Other resins developed for the production of protected peptide segments or fragments by Fmoc-SPPS are susceptible to similar problems. Most notably, prior resins flaws include the irreversible attachment of tryptophan to the support resin and the alkylation of various amino acids when the product is being cleaved from the solid support matrix.

There has been a continuing need for resins usable in Fmoc SPPS which result in higher yields, and higher purity, and which are applicable to the building of all sequences of both naturally occurring and unnatural amino acids, as well as other molecules containing carboxylic acids moieties.

SUMMARY OF THE INVENTION

The present invention provides three resins each of which provides a unique functional handle unto which protected amino acids and other molecules possessing a free carboxylic acids moiety can be attached.

The first resin (Resin #1) takes the formula of 4-hydroxy-3-methoxy-benzoyl alcohol (HMBA) attached to a polystyrene-dvb copolymer and is a general purpose resin for routine Fmoc-SPPS. It is far less expensive to produce than the standard p-alkoxy benzoyl alcohol resin used for Fmoc-SPPS since the starting material, vanillyl alcohol is readily and inexpensively available in large quantities. The finished synthetic peptide can be cleaved from the resin using 25% TFA in dichloromethane (DCM) which is a significant improvement over the 95% TFA required to cleave products from p-alkoxy benzoyl alcohol resin. The HMBA resin may be derivatized or loaded with an amino acid or other carboxylic acid containing molecule.

The second resin (Resin #2) may be termed trityl alcohol attached to a polystyrene-dvb matrix. The second resin is a very dilute acid susceptible resin for the production of protected peptide fragments by Fmoc-SPPS. The finished protected peptides are cleaved from the support matrix with 15% acetic acid and 85% DCM. The elimination of TFA during this desirable cleaving step is a significant, and unexpected property of Resin #2. The level of substitution of the starting material and the yield of synthetic peptides using such material is quiet high.

The third resin (Resin #3) is specifically designed for the production of peptide amides by Fmoc-SSPS. Resin #3 is a trityl amine linked to a polystyrene-dvb matrix. Such trityl amine resin may be loaded with an amino acid and employed in peptide synthesis using the Fmoc-SSPS strategy. The trityl amine resin may also be loaded with other carboxyl acid containin molecules to yield carboxyl amides. The peptide amide may be cleaved from the resin using 25% TFA in DCM without multistep syntheses of linker intermediates.

It may be apparent that a novel and useful group of resins employed in Fmoc-SPPS synthesis has been described.

It is therefore an object of the present invention to provide solid support resins for Fmoc-SSPS synthesis which are applicable for all 20 of the naturally occurring L-amino acids, the unnatural D-amino acids, and for any other molecule which contains a carboxylic acid moiety.

It is another object of the present invention to provide a solid support resin for Fmoc-solid phase peptide synthesis which results in high yield of synthetic polypeptides.

Another object of the present invention is to provide solid support resins for Fmoc-solid phase peptide synthesis which eliminates undesirable side reactions during the attachment of the first amino acid to the solid support matrix.

Yet another object of the present invention is to provide solid support resins for Fmoc-solid phase peptide synthesis which requires a decreased amounts of solvent in the washing steps during the peptides building processes compared to prior art resins.

Yet another object of the present invention is to provide solid support resins for Fmoc-solid phase peptide synthesis which are relatively inexpensive and easy to manufacture.

The invention possesses other objects and advantages especially as concerns particular characteristics and features thereof which will be apparent as the specification continues.

DESCRIPTION OF THE PREFERRED EMBODIMENTS

Resin #1 may be prepared by adding the Merrifield resin of the prior art to the vanillyl alcohol or a derivative thereof by the following reaction:

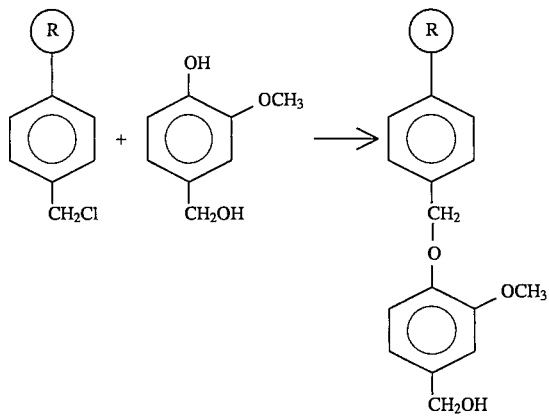

The R with a circle around it indicates a styrene-divinylbenzene copolymer in a gel form or a pellicular form which is suitable for flow synthesis.

Resin #1 may be represented by the following formulae:

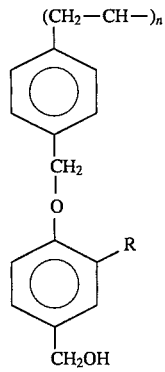

where: "n" is the basic unit of the resin matrix, R is a methyl, ethyl, or lower alkyl group having (7) carbons or less. R may also stand for methoxy, ethoxy, or lower alkoxy group having (7) carbons or less.

Treating the above resin with an Fmoc-amino acid group loads or derivatizes the subject resin. Such addition takes place in the presence of carbonyldiimidazol (CDI) and DCM. The product is collected by filtration after an incubation period. The following formulae represents the derivatized resin #1.

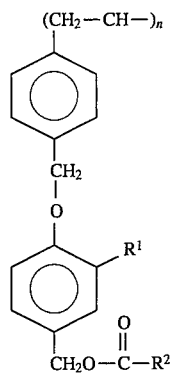

where "n" is the basic unit of the resin matrix, $R^1$ an alkyl or alkoxy group, and where $R^2$ is an amino acid moiety or other carboxylic acid containing molecule. It has been discovered that the derivatized HMBA resin (Resin #1) may be cleaved using 25% TFA in DCM which achieves a significant improvement over the 95% TFA required by the prior art, in that undesirable side reactions are virtually eliminated.

Resin #2 is formed by the reaction between polystyrene-dvb copolymer and benzoyl chloride in the presence of aluminum chloride and dichloroethane (DCE) to produce a keto resin. Such resin is then formed into an alcohol by a Grignard reaction in the presence of tetrahydrofuran (THF) according to the following reaction:

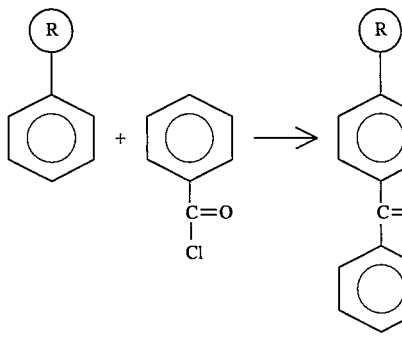

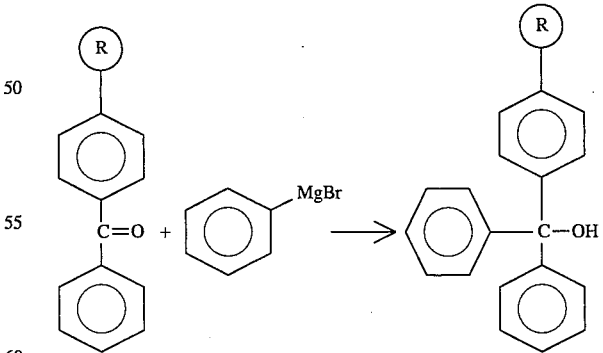

Resin #2 is a very dilute acid susceptible resin which may be employed for the production of protected peptide fragments by Fmoc-SPPS. 15% acetic acid in 85% DCM, rather than TFA, may be used to cleave the finished protected peptides from the support matrix. Resin #2 may be shown by the following formula:

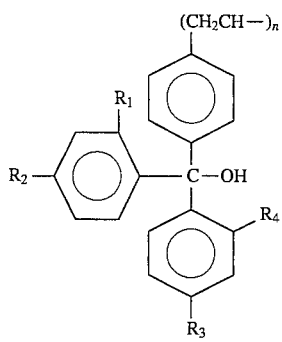

where "n" is the basic unit of the resin matrix, $R_1$, $R_2$, $R_3$, and/or $R_4$ is either hydrogen, methyl, ethyl, or lower alkyl groups of (7) carbons or less, methoxy, ethoxy, or lower alkoxy groups of (7) carbons or less. In its derivatized or loaded form, resin 2 may be represented by the formula:

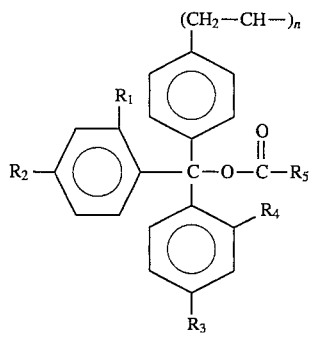

where $R_5$ is an amino acid moiety or other carboxylic acid containing molecule. It should be noted that the alcohol functional group of Resin #2 must be converted to a chloride prior to loading, which will be described in detail hereinafter.

Resin #3 is used specifically for the production of peptide amides by Fmoc-SPPS and is prepared according to the following reaction where a trityl chloride resin is converted to the trityl amine resin (Resin #3) in the presence of anhydrous ammonia and DCM:

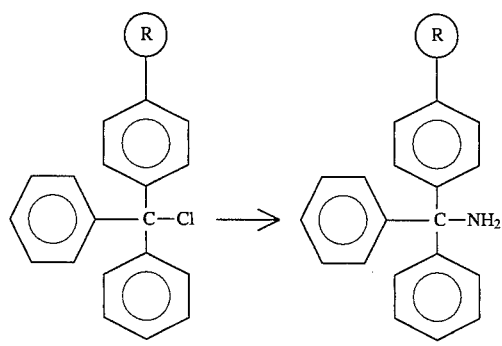

It should be noted that the trityl chloride resin shown above may be gathered from the derivatization process with respect to resin #2 under the following reaction by treating trityl alcohol resin with acetylchloride in the presence of DCM:

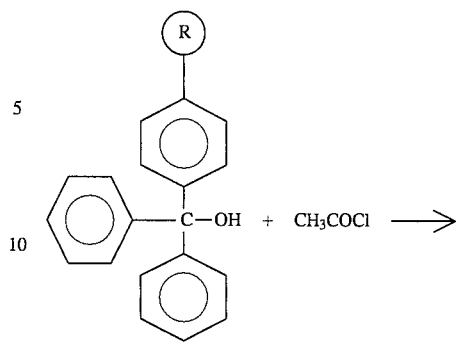

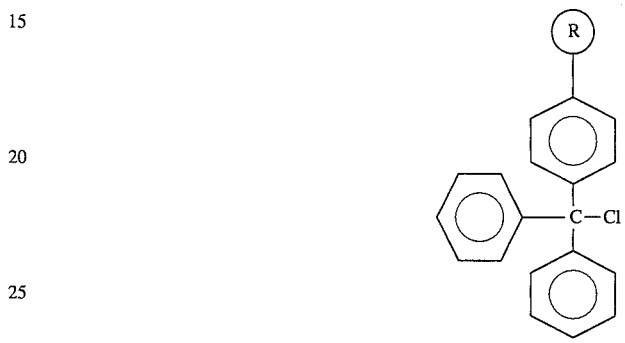

The trityl chloride resin may be loaded with the Fmoc-amino acid group or converted to the trityl amine resin above shown. The trityl amine resin (Resin #3) may be represented by the following formula:

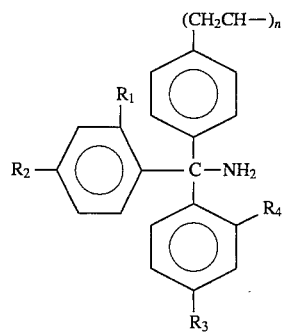

where "n" is the basic unit of the resin matrix, $R_1$, $R_2$, $R_3$, and/or $R_4$, are hydrogen, methyl, ethyl or other lower alkyl group, with less than (7) carbons, methoxy, ethoxy or other lower alkoxy group, with less than (7) carbons.

In its derivatized or loaded state, resin #3 may be represented by the following formula:

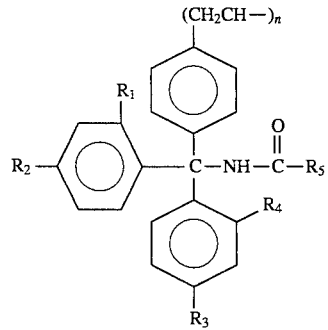

where $R_5$ is an amino acid moiety or other carboxylic acid containing molecule.

The present invention is illustrated by the following examples, but is not deemed to be restricted thereby. Abbreviations appearing therein are ones normally used in the field of solid phase peptide synthesis.

EXAMPLE 1

This example describes the production, derivatization and cleavage of resin #1 hereinbefore described.

6.0 gm of chloromethylated polystyrene-DVB copolymer at 4.15 meq of chloride per gram of resin was swollen in 50 ml of either dimethylacetamide (DMA) or dimethylformamide (DMF). 11.24 gm of 4-hydroxy-3-methoxy benzyl alcohol (HMBA or vanillyl alcohol) was dissolved in 20 ml of DMA. This solution was added to the swollen resin and mixed. 3.94 gm of sodium methoxide was then added to the suspension and incubated at 65° C. for 8 hours and then steadily mixed overnight at room temperature. The resulting HMBA resin was collected by filtration, washed with DMF, twice with dichloromethane (DCM), once with methanol, and again, twice with DCM. The washed filtrate was dried in an oven at 45° Centigrade. The resulting yield was 11.63 gm of derivitized HMBA resin which calculated to a weight gain of 5.63 gm. It was determined that 36.5 mmoles of the HMBA was attached to the polystyrene-DVB copolymer. Thus, the final product included 2.7 mmole/gm of functional units. 1.0 gm of this product was loaded using exemplar Fmoc-phenylalanine as follows. 2.0 gm of carbonyldiimidazol (12.3 mmole) was dissolved with 2.6 gm of Fmoc-phenylalanine (6.7 mmole) in 10 ml of DCM, mixed thoroughly, and preincubated at room temperature for 10–15 minutes. This mixture was then added the HMBA resin, and the suspension was incubated overnight at room temperature (21° C.). The product was then collected by filtration, washed twice with DCM, once with methyl alcohol, twice with DCM, and dried in an oven at 35° C. The level of substitution was determined on a 10 mg sample of the product by cleaving off the Fmoc group with 1.0 ml of 20% pyrrolidine in DCM, filtering off the resin, and diluting the volume to 10 ml. The optical density of a 1:10 dilute sample was then measured. This figure was then divided by the molar extension coefficient$\times 10^{-3}$. The resulting value represents the mmole/gm of Fmoc-amino acid attached to the resin and equals the level of substitution achieved. In this illustrative portion of Example I, 1.24 mmole of Fmoc-phenylalanine per gram of resin was achieved. The following Table I illustrates the level of substitution achieved with other Fmoc-amino acids using similar techniques to the above described technique employed with Fmoc-phenylalanine.

TABLE I

Loading of HMBA resin (Resin #1) with Fmoc-Amino Acids

| Fmoc-Amino Acid | Level of Substitution Achieved in mmole/gm |
| --- | --- |
| Fmoc-Ala | 0.84, 0.69 & 0.50 |
| Fmoc-Gly | 0.68, 0.52 & 0.73 |
| Fmoc-Gln(Trt) | 0.35 |
| Fmoc-Glu(o-t-But) | 0.34 |
| Fmoc-Leu | 0.55, 0.27, 1.36 & 0.83 |
| Fmoc-Phe | 1.24 & 0.69 |
| Fmoc-Pro | 0.47 |
| Fmoc-Ser(o-t-But) | 0.70 & 0.39 |
| Fmoc-Tyr(o-t-But) | 0.49 |
| Fmoc-Val | 0.77 & 0.43 |

The loaded resins above identified can be used in Fmoc-SPPS and the cyclic additions of amino acids through the use of preformed symmetric anhydrides, DIPCDI/HOBt, BOP/HOBt or various other coupling methods. Subsequent to building the desired peptide sequence, peptide (with a free carboxyl terminal) is cleaved from the support resin by treating the peptide-resin with 100 ml of 25% TFA in DCM per mmole of peptide. The following Table II illustrates the time course for cleavage of various Fmoc-amino acids from the support resin. The free synthetic peptide is isolated and used as desired.

TABLE II

Cleavage of Fmoc-Amino Acids from HMBA Resin with 25% TFA.

| Fmoc-Amino Acid | Length of Incubation | Mmole/gm |
| --- | --- | --- |
| Fmoc-Leu | 10 min. | 0.22 |
|  | 20 min. | 0.22 |
|  | 30 min. | 0.28 |
|  | 60 min. | 0.38 |
|  | 120 min. | 0.23 |
| Fmoc-Val | 10 min. | 0.36 |
|  | 20 min. | 0.36 |
|  | 30 min. | 0.32 |
|  | 60 min. | 0.42 |
|  | 120 min. | 0.45 |
| FMOC-Gln(Trt) | 10 min. | 0.25 |
|  | 20 min. | 0.30 |
|  | 30 min. | 0.26 |
|  | 60 min. | 0.24 |
|  | 120 min. | 0.28 |

EXAMPLE 2

Production, derivitization, and cleavage of resin #2 (trityl alcohol resin).

50 gm of polystyrene-DVB copolymer was swollen in 400 ml of dichloroethane (DCE) or DCM and the suspension chilled to −6° C. 56 mm of benzyol chloride and 64 gm of aluminum chloride were suspended in 100 ml of the same solvent and added dropwise to the suspended resin with constant mixing. After the dropwise addition was completed, the suspension was allowed to come to room temperature and the keto resin formation continued overnight with constant mixing. The resulting keto-resin was collected by filtration, washed twice with DCM, once with methanol, again, twice with DCM and dried in an oven at 45° C. The yield was 82 grams of keto-resin at 3.75 mmole/gm. 5 gm of keto-resin was suspended in 50 ml of tetrahydrofuran (THF) and 15 ml of 3M phenylmagnesium bromide in ether was added to the suspension with constant mixing. The Grignard reaction was incubated overnight at room temperature to yield trityl alcohol resin (Resin #2) which was collected by filtration, washed twice with DCM, once with methanol, again, twice with DCM, and dried in an oven at 35° C. The trityl alcohol resin is then converted to a chloride prior to loading. The dried trityl alcohol resin from the Grignard reaction was swollen in 50 ml of toluene and 10 ml of acetyl chloride (140 mmole) was added and incubated overnight at room temperature to convert the functional group from a hydroxyl to a chloride. The trityl chloride resin was collected by filtration washed and dried as the trityl alcohol resin hereinbefore. To load the trityl chloride resin 3 grams of the same was employed. 3.87 gm of Fmoc-phenyalanine (10 mmole) or other carboxylic acid containing molecule and an equivalent amount of diisopropylethylamine (DIEA) disolved in DCM was added, and the suspension incubated overnight at room temperature (21° C.). The product was collected by filtration washed and dried in the same manner as the trityl alcohol resin hereinbefore described. The level of substitution was determined on a 10 mg sample by cleaving off the Fmoc group with 1.0 ml of 20% pyrrolidine in DCM, filtering off the resin, adjusting the volume to 10 ml measuring the optical density of a 1:10 dilute sample and dividing the OD by the molar extinction coefficient×10$^{-3}$. The resulting quantity represents the mmole per gram of Fmoc-amino acid attached to the resin and, thus, equals the level of substitution achieved. Table III below illustrates the level of substitution achieved with various Fmoc amino acids using resin #2:

TABLE III

Loading of Trityl Alcohol Resin (Resin #2) with Fmoc-Amino Acids.

| Fmoc-Amino Acid | Level of Substitution Achieved in mmole/gm |
|---|---|
| Fmoc-Ala | 0.41 |
| Fmoc-Cys(Trt) | 0.95 |
| Fmoc-Cys(Acm) | 0.46 |
| Fmoc-Asp(o-t-But) | 0.95 |
| Fmoc-Glu(o-t-But) | 0.34 |
| Fmoc-Phe | 0.95 & 0.62 |
| Fmoc-Gly | 0.80, 1.00 & 0.60 |
| Fmoc-His(Trt) | 0.81 |
| Fmoc-Ile | 1.03 |
| Fmoc-Lys(Boc) | 0.85 |
| Fmoc-Leu | 0.88 & 0.79 |
| Fmoc-Met | 0.83 |
| Fmoc-Asn | 0.76 |
| Fmoc-Asn(Trt) | 0.65 |
| Fmoc-Pro | 0.84 |
| Fmoc-Gln | 0.53 |
| Fmoc-Gln(Trt) | 0.42 |
| Fmoc-Arg(Mtr) | 0.31 |
| Fmoc-Arg(Pmc) | 0.31 |
| Fmoc-Ser(o-t-But) | 0.85 |
| Fmoc-Thr(o-t-But) | 0.85 |
| Fmoc-Val | 0.91 |
| Fmoc-Trp | 0.66 |
| Fmoc-Tyr(o-t-But) | 0.82 |

The derivatized or loaded resin was then ready for use in Fmoc-SPPS and the cyclic addition of amino acids using preformed symmetric anhydrides with an equivalent of DIEA or BOP/HOBt/DIEA coupling. Various amino acids were attached and cleaved from the support resin by treatment of the peptide-resin with 200 ml of 15% acetic acid and DCM per mole of peptide. Table IV illustrates the time course for cleavage of various Fmoc-amino acids from the support resin.

TABLE IV

| Fmoc-Amino Acid | Length of Incubation | Mmole/gm |
|---|---|---|
| Fmoc-Phe | 10 min. | 0.67 |
|  | 20 min. | 0.59 |
|  | 30 min. | 0.59 |
|  | 60 min. | 0.61 |
|  | 120 min. | 0.60 |
| Fmoc-Leu | 10 min. | 0.83 |
|  | 20 min. | 0.67 |
|  | 30 min. | 0.66 |
|  | 60 min. | 0.78 |
|  | 120 min. | 0.75 |
| Fmoc-Gly | 10 min. | 0.60 |
|  | 20 min. | 0.54 |
|  | 30 min. | 0.59 |
|  | 60 min. | 0.74 |
|  | 120 min. | 0.52 |

The trityl chloride resin produced and described in Example II was used as the starting material. The chloride group was converted to a amine group by swelling the trityl chloride resin in DCM and anhydrous ammonia was bubbled through the suspension overnight. The trityl amine resin was collected by filtration, washed, and dried according to the process described in Example II. 1.0 gm of the trityl amine resin was loaded with Fmoc amino acids. As an example, 3.1 grams of Fmoc-phenylalanine (8.0 mmole), an equivalent amount of diisopropylcarbodiimide (DIPCDI), and an equivalent amount of hydroxybenzotriazole (HOBt) were added together, dissolved in DMF, and the resulting suspension incubated 4–6 hours at room temperature (21° C.). The product was collected by filtration, washed, and dried by the process heretofore described. The level of substitution was determined on a 10 mg sample by cleaving off the Fmoc group with 1.0 ml of 20% pyrrolidine in DCM, filtering off the resin, adjusting the volume to 10 ml, and measuring the optical density (OD) of a 1:10 dilute sample, and dividing the OD by the molar extinction coefficient×10$^{-3}$. The resulting number represents the mmole/gm of Fmoc-amino acid attached to the resin and equals the level substitution achieved. Table V illustrates the level of substitution achieved with various Fmoc-amino acids prepared by using resin #3:

TABLE V

Loading of Trityl Amine Resin (Resin #3) with Fmoc-Amino Acids.

| Fmoc-Amino Acid | Level of Substitution Achieved in mmole/gm |
|---|---|
| Fmoc-Met | 0.15 |
| Fmoc-Phe | 1.30 |
| Fmoc-Pro | 0.35 |
| Fmoc-Asn | 0.71 |

Again such loaded resins can be used in Fmoc-SPPS and the cyclic addition of amino acids using methods heretofore described in Examples I and II. Peptide sequences built using the resin of this Example were cleaved from the support resin by treating the peptide resin with 100 ml of 25% TFA in DCM per mmole of peptide. The cleaved entity is a free peptide with a carboxyl amide terminal. Table VI illustrates the time course for cleavage of various Fmoc-Amino Acid-Amides from the support resin.

TABLE VI

Cleavage of Fmoc-Amino Acid Amides from Trityl Amine Resin with 25° TFA in DCM.

| Fmoc-Amino Acid | Length of Incubation | Mmole/gm |
|---|---|---|
| Fmoc-Pro—NH$_2$ | 10 min. | 0.19 |
|  | 20 min. | 0.13 |
|  | 30 min. | 0.19 |
|  | 60 min. | 0.19 |
|  | 120 min. | 0.16 |
| Fmoc-Asn—NH$_2$ | 10 min. | 0.88 |
|  | 20 min. | 0.62 |
|  | 30 min. | 0.75 |
|  | 60 min. | 0.42 |
|  | 120 min. | 0.39 |

EXAMPLE 3

Production, Derivatization, and Cleavage of Resin #3 Tritylamine Resin.

EXAMPLE 4

Employing resin #1 of Example I (HMBA Resin), a 12 mer having the following formula was built:

Ac-Tyr-Cys-Ala-Pro-Leu-Lys-Pro-Ala-Lys-Ser-Ala 200 mgm of Fmoc-Ala-HMBA resin, of Example 1 at a level of substitution of 0.5 mmole/gm (0.1 mmole of substituted resin) was used. The remaining eleven amino acids of the present 12 mer were added in cyclic fashion. The addition of each Fmoc-Amino Acid was achieved using a four fold molar excess of the individual Fmoc-Amino Acids, HOBt, and DIPCDI during coupling cycle. The Fmoc-protecting group was removed using 20% pyrrolidine in DMF during the deprotection step of each cycle. After the amino terminal tyrosine was deprotected, the amino terminus was acetylated using acetic anhydride and triethylamine. The synthetic peptide was cleaved from support resin and the side chains of the trifunctional amino acids were deprotected simultaneously by treating the peptide-resin with 25% TFA, 4% water and DTT in DCM. The crude peptide was partially purified by gel filtration in 25% acetic acid and yielded 126 mgm of peptide. Based on a molecular weight of 1208.6, the yield of peptide was 104.2%. The partially pure peptide was purified to homogeneity by preparative HPLC, which yielded 82.5 mgm of pure peptide (68.3% overall yield). Amino acid analysis of the peptide yielded the following results shown in Table VII below.

TABLE VII

| Residue | Theory | Found |
| --- | --- | --- |
| Ala | 3 | 2.9 |
| Tyr | 1 | 1.0 |
| Lys | 2 | 2.0 |
| Pro | 2 | 2.0 |
| Cys | 1 | present |
| Ser | 1 | 0.9 |
| Leu | 1 | 1.0 |

EXAMPLE 5

Utilizing the HMBA resin of Example I (Resin #1) the following peptide was constructed:

Ser-Tyr-Thr-Asn-Pro-Glu-Phe-Val-Ile-Asn-Val 465 mgm of Fmoc-Val-HMBA resin at a level of substitution of 0.43 mmole/gm (0.2 mmole of substituted resin) was employed. The cyclic addition of each Fmoc-amino acid was achieved using a fourfold molar excess of the individual Fmoc-amino acids, HOBt, and DIPCDI during each coupling cycle. The Fmoc protecting group was removed using 20% pyrrolidine in DMF during the deprotection step of each cycle. The peptide was cleaved from the support resin and the side chains of the trifunctional amino acids were deprotected simultaneously by treating the peptide-resin with 25% TFA, 4% water, and 1% DTT in DCM. The crude peptide was partially purified by gel filtration in 25% acetic acid and yielded 256 mgm of peptide. Based on a molecular weight of 1282.3, the yield was 99.8%. The partially pure peptide was purified to homogeneity by preparative HPLC and yielded 119 mgm of pure peptide (46.4% overall yield). Amino acid analysis of the peptide yielded the following results which is represented in Table VIII below.

TABLE 6

| Residue | Theory | Found |
| --- | --- | --- |
| Asx | 2 | 2.1 |
| Glx | 1 | 1.0 |
| Tyr | 1 | 1.0 |
| Thr | 1 | 0.9 |
| Pro | 1 | 1.0 |
| Ile | 1 | 1.1 |
| Phe | 1 | 1.0 |
| Ser | 1 | 0.9 |
| Val | 2 | 2.0 |

EXAMPLE 6

Utilizing the HMBA resin (Resin 1) of Example I, the following peptide was constructed:

Ser-Phe-Val-Asn-Ser-Glu-Phe-Leu-Lys-Pro-Glu-Val-Lys-Ser 384 mgm of Fmoc-Ser(o-t-But)-HMBA resin at 0.39 mmole/gm (0.15 mmole of substituted resin) was used. The cyclic addition of each Fmoc-amino acid was achieved using a four fold molar excess of the individual Fmoc-amino acids, HOBt, and DIPCDI during each coupling cycle. The Fmoc protecting group was removed using 20% pyrrolidine in DMF during the deprotection step of each cycle. The peptide was cleaved from the support resin and the side chains of the trifunctional amino acids were deprotected simultaneously by treating the peptide-resin with 25% TFA, 4% water, and 1% DTT in DCM. The crude peptide was partially purified by gel filtration in 25% acetic acid and yielded 231 mgm of peptide. Based on a molecular weight of 1610.9, the yield was 95.6%. The partially pure peptide was purified to homogeneity by preparative HPLC and yielded 172 mgm of pure peptide (70.9% overall yield). Amino acid analysis of the peptide yielded the following results which is shown in Table IX:

TABLE IX

| Residue | Theory | Found |
| --- | --- | --- |
| Asx | 1 | 1.0 |
| Glx | 2 | 1.9 |
| Lys | 2 | 2.0 |
| Pro | 1 | 1.0 |
| Phe | 2 | 2.0 |
| Ser | 3 | 2.6 |
| Val | 2 | 2.1 |
| Leu | 1 | 1.0 |

EXAMPLE 7

The following protected peptide was constructed using the trityl alcohol resin of Example II (Resin 2):

Fmoc-Cys(Trt)-Ser(o-t-But)-Asn-Leu-Ser(o-t-But)-Thr(o-t-But)-Cys(Trt)-Val-Leu-Gly 100 mgm of Fmoc-Gly-Trityl resin at 1.00 mmole/gm (0.1 mmole of substituted resin) was used. The cyclic addition of each Fmoc-amino acid was achieved using an equivalent HOBt, a three fold molar excess of the individual Fmoc-amino acids and BOP, and a 6 fold molar excess of DIEA during each coupling cycle. The Fmoc-protecting group was removed using 20% pyrrolidine in DMF during the deprotection step of each cycle. However, the last Fmoc protecting group on the amino acid terminal residue was not removed. Therefore, the amino terminus as well as all the side chains of the trifunctional amino acids were still protected when the synthesis of this peptide was complete. The fully protected peptide was cleaved from the support resin with 15% acetic acid in DCM. The protected peptide was collected, the acetic acid extracted into water 3 times, the solvent removed by rotary evaporation, and the product dried over $P_2O_5$ under vacuum. 165 mgm of protected peptide was recovered. Based on a molecular weight of 1805.0 for the fully protected peptide, the yield was 91.4%. A sample of the protected peptide is treated with 20% pyrrolidine in DCM to remove the Fmoc-protecting group, and the sample was hydrolyzed for amino acid analysis. Amino acid analysis of the sample yielded the following results which is shown in Table X.

TABLE X

| Residue | Theory | Found |
|---------|--------|-------|
| Asx | 1 | 1.0 |
| Thr | 1 | 0.9 |
| Cys | 2 | present |
| Ser | 2 | 1.8 |
| Gly | 1 | 1.0 |
| Val | 1 | 1.0 |
| Leu | 2 | 2.1 |

EXAMPLE 8

The following peptide was constructed using the Trityl alcohol resin of Example II (Resin 2):

Fmoc-Glu(o-t-But)-Thr(o-t-But)-Leu-Pro-Gln-Gly 200 mgm of Fmoc-Gly-Trityl resin at 1.0 mmole/gm (0.2 mmole of substituted resin) was used. The cyclic addition of each Fmoc-amino acid was achieved using an equivalent of HOBt, a three fold molar excess of the individual Fmoc-amino acids and BOP, and a six fold molar excess of DIEA during each coupling cycle. The Fmoc-protecting group was removed using 20% pyrrolidine in DMF during the deprotection step of each cycle. However, the last Fmoc-protecting group on the amino terminal residue was not removed. Therefore, as with Example VII, the amino terminus as well as all the side chains of the trifunctional amino acids were still protected when synthesis of the peptide was complete. The fully protected peptide was cleaved from the support resin with 15% acetic acid in DCM. The protected peptide was collected, the acetic acid extracted into water 3 times. The solvent was removed by rotary evaporation and the product dried over $P_2O_5$ under vacuum. 177 mgm of protected peptide was recovered. Based on a molecular weight of 960.8 for the fully protected peptide, the yield was 92.2%. A sample of the protected peptide was treated with 20% pyrrolidine in DCM to remove the Fmoc-protecting group, and the sample hydrolyzed for amino acid analysis. The amino acid analysis yielded the following results which is shown in Table XI.

TABLE XI

| Residue | Theory | Found |
|---------|--------|-------|
| Glx | 2 | 2.0 |
| Thr | 1 | 0.9 |

TABLE XI-continued

| Residue | Theory | Found |
|---------|--------|-------|
| Pro | 1 | 1.0 |
| Gly | 1 | 1.0 |
| Leu | 1 | 1.0 |

EXAMPLE 9

Employing the Trityl Amine resin of Example III (Resin #3) the following peptide was constructed:

Lys-Lys-Tyr-Leu-Glu-Ser-Leu-Met-NH$_2$ 170 mgm of Fmoc-Met-Trityl Amine resin at 0.15 mmole/gm (0.025 mmole of substituted resin) was used. The cyclic addition of each Fmoc-amino acid was achieved using a four fold molar excess of the individual Fmoc-amino acids, HOBt and DIPCDI during each coupling cycle. The Fmoc-protecting group was removed using 20% pyrrolidine in DMF during the deprotection step of each cycle. The peptide was cleaved from the support resin and the side chains of the trifunctional amino acids were deprotected simultaneously by treating the peptide-resin with 25% TFA, 4% water, and 1% DTT in DCM. The crude peptide was partially purified by gel filtration in 25% acetic acid and yielded 24 mgm of peptide. Based on a molecular weight of 1010.4, the yield was 95%. The partially pure peptide was purified to homogeneity by preparative HPLC and yielded 20 mgm of pure peptide (79.2% overall yield). Amino acid analysis yielded the following result is shown in the following Table XII:

TABLE XII

| Residue | Theory | Found |
|---------|--------|-------|
| Glx | 1 | 1.0 |
| Met | 1 | 1.0 |
| Tyr | 1 | 1.0 |
| Lys | 2 | 2.0 |
| Ser | 1 | 0.9 |
| Leu | 2 | 2.0 |

EXAMPLE 10

The following peptide was constructed utilizing the Trityl Amine resin of Exampe III (Resin 3): Phe-Met-Arg-Phe-NH$_2$ 260 mgm of Fmoc-Phe-Trityl Amine resin at 1.30 mmole/gm (0.20 mmole of substituted resin) was used. The cyclic addition of each Fmoc-amino acid was achieved using a four fold molar excess of the individual Fmoc-amino acids, HOBt and DIPCDI during each coupling cycle. The Fmoc-protecting group was removed using 20% pyrrolidine in DMF during the deprotection step of each cycle. The peptide was cleaved from the support resin with 25% TFA and 1.0% DTT in DCM for 60 minutes. The crude peptide was then treated with 50% TFA and 10% thioanisole in DCM overnight to remove the Pmc blocking group from the side chain of arginine. The peptide was partially purified by gel filtration in 25% acetic acid and yielded 122 mgm of peptide. Based on a molecular weight of 598.8, the yield was 101.8%. The partially pure peptide was purified to homogeneity by preparative HPLC and yielded 107 mgm of pure peptide (89.3% overall yield). Amino acid analysis yielded the follow results which is shown by Table XIII below.

TABLE XIII

| Residue | Theory | Found |
|---------|--------|-------|
| Met | 1 | 1.0 |
| Phe | 2 | 2.0 |
| Arg | 1 | 1.0 |

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A polymeric resin for use in solid phase synthesis consisting essentially of the formulae:

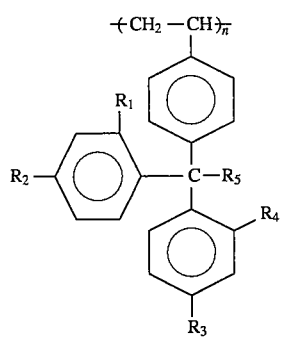

where $R_1$, $R_2$, $R_3$, and $R_4$ selectively hydrogen an alkoxy, and an alkyl group and $R_5$ is a group capable of forming a carbon bond for amino acid moieties or amino acid moieties bonded to a protecting group and where $R_5$ is a chloride.

2. A polymeric resin for use in solid phase synthesis consisting essentially of the formulae:

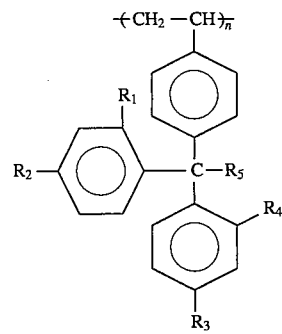

where $R_1$, $R_2$, $R_3$, and $R_4$ is selectively hydrogen, and an alkyl group and $R_5$ is a group capable of forming a carbon bond for amino acid moieties or amino acid moieties bonded to a protecting group, and where $R_5$ is an amino group.

3. The polymeric resin of claim 1 where the carbon bond for the amino acid moiety is represented by the formula:

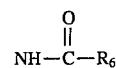

and where $R_6$ is such amino acid moiety.

4. The polymeric resin of claim 2 where the carbon bond for the amino acid moiety bonded to a protecting group is represented by the formula:

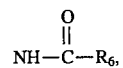

where $R_6$ is such amino acid moiety linked to a protecting group.

5. The polymeric resin of claim 2 in which the basic resin matrix is polystyrene cross-linked with divinylbenzene.

6. The polymeric resin of claim 1 where the carbon bond for the amino acid moiety is represented by the formula:

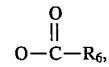

where $R_6$ is an amino acid moiety.

7. The polymeric resin of claim 2 where the carbon bond for the amino acid moiety bonded to a protecting group is represented by the formula:

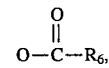

where $R_6$ is an amino acid moiety is linked to a protecting group.

* * * * *